United States Patent [19]

de Vries

[11] 4,269,790

[45] May 26, 1981

[54] HYDROCARBYLETHYL SULFONYL FLUORIDE

[75] Inventor: Louis de Vries, Greenbrae, Calif.

[73] Assignee: Chevron Research Company, San Francisco, Calif.

[21] Appl. No.: 49,995

[22] Filed: Jun. 18, 1979

Related U.S. Application Data

[62] Division of Ser. No. 889,314, Mar. 23, 1978, abandoned.

[51] Int. Cl.$^3$ .......................................... C07C 143/70
[52] U.S. Cl. .............................. 260/543 F; 252/47.5; 252/48.4
[58] Field of Search .................. 260/543 F; 526/243; 525/276; 252/48.4

[56] References Cited

U.S. PATENT DOCUMENTS

| | | | |
|---|---|---|---|
| 2,114,577 | 4/1938 | Schrader et al. | 260/543 F |
| 2,801,991 | 8/1957 | Hedrick | 526/243 |
| 2,846,472 | 8/1958 | Tiers | 260/543 F |
| 3,050,556 | 8/1962 | Tiers | 260/543 F |
| 3,128,307 | 4/1964 | Zorn et al. | 252/48.4 |
| 4,005,138 | 1/1977 | Plattner et al. | 260/543 F |

*Primary Examiner*—Natalie Trousof
*Assistant Examiner*—L. Hendriksen
*Attorney, Agent, or Firm*—D. A. Newell; V. J. Cavalieri

[57] ABSTRACT

Hydrocarbylethyl sulfonyl fluorides in which the hydrocarbyl substituent contains at least 3 carbon atoms, can be prepared by reacting 2-mercaptoethanol with chlorine to form chloroethyl sulfonyl chloride which is treated with aqueous potassium fluoride to yield chloroethyl sulfonyl fluoride, followed by treatment with magnesium oxide to yield vinyl sulfonyl fluoride. The vinyl sulfonyl fluoride is adducted to a hydrocarbyl substituent precursor, such as an olefin or halogenated olefin. A representative compound is polyisobutenyl sulfonyl fluoride. The hydrocarbylethyl sulfonamide products for which the hydrocarbylethyl sulfonyl fluorides are intermediates are useful as additives for lubricating oils.

4 Claims, No Drawings

HYDROCARBYLETHYL SULFONYL FLUORIDE

This is a division of application Ser. No. 889,314, filed Mar. 23, 1978, now abandoned.

BACKGROUND OF THE INVENTION

Field of the Invention

This invention relates to processes for preparing hydrocarbylethyl sulfonyl fluorides. The higher-molecular-weight compounds are useful as intermediates for lubricating oil additives. The intermediate-molecular-weight compounds are useful as detergent intermediates, and the lower-molecular-weight compounds are useful intermediates in the preparation of agricultural and medicinal compounds. This invention further relates to hydrocarbylethyl sulfonyl fluorides, methods for their preparation, and lubricating oil additives and compositions prepared from them.

Dispersants for use in lubricating oils have become a necessity for use in modern engines. One such class of dispersants is hydrocarbylethyl sulfonamides. A method for their preparation via a new intermediate enables these sulfonamides to be easily produced.

SUMMARY OF THE INVENTION

Hydrocarbylethyl sulfonyl fluorides containing a total of at least 5 carbon atoms can be prepared by reacting vinyl sulfonyl fluoride with an unsaturated hydrocarbyl substituent precursor as defined below. The hydrocarbylethyl sulfonyl fluorides containing at least 20 carbon atoms can be used to prepare lubricating oil additives having dispersant activity by reaction with an organic compound containing at least one

—NH group.

The hydrocarbylethyl sulfonyl fluoride containing from 5 to 25 carbon atoms can be used to prepare water-soluble detergents by saponification with a base such as sodium hydroxide. The hydrocarbylethyl sulfonyl fluoride contaning from 5 to 10 carbon atoms can be used to prepare medicinal or agricultural chemicals by reaction with low-molecular-weight primary or secondary amides or by reaction with low-molecular-weight alcohols.

The primary product of the reaction between the hydrocarbylethyl sulfonyl fluoride and the organic compound having at least one

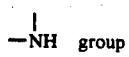
—NH group is a sulfonamide. Throughout the remainder of this discussion the lubricating oil additives prepared from the hydrocarbylethyl sulfonyl fluoride and the organic compound containing at least one

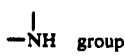
—NH group will be generally described as sulfonamides, even though the reaction products may comprise a mixture of sulfonamides and other products.

DETAILED DESCRIPTION OF THE INVENTION

The hydroxycarbylethyl sulfonyl fluorides may have either of the following formulas: but primarily I:

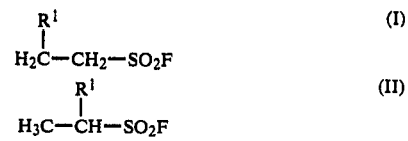

wherein $R^1$ represents a hydrocarbyl substituent containing at least 3 carbon atoms. For use as an intermediate in the preparation of lubricating oil additives, $R^1$ will generally contain at least 25 and not more than 250 carbon atoms, preferably from about 35 to 250 carbon atoms, and most preferably from about 50 to 150 carbon atoms. For use as an intermediate in the preparation of water-soluble detergents, $R^1$ will generally contain at least 3 and not more than 23 carbon atoms, preferably from 8 to 18 carbon atoms, and most preferably 14 to 16 carbon atoms.

When used as an intermediate for lubricating oil additives, the hydrocarbyl substituent should be substantially saturated. By "substantially saturated" is meant that at least about 80% of the total number of carbon-to-carbon covalent linkages are saturated linkages or, in other words, that no more than about 1 to 3 olefinic double bonds are present in the hydrocarbon. An excessive proportion of unsaturated linkages renders the molecules susceptible to oxidation, degradation and polymerization and results in products unsuitable for use in hydrocarbon oils in many applications.

The hydrocarbyl substituent may contain prior substituents provided that the polar substituents do not react under the conditions of saponification or in the formation of sulfonamides. Suitable polar substituents are exemplified by chloro, keto, alkoxy, etc. Preferably, less than 10% by weight of the hydrocarbyl portion of the molecule is polar groups.

The hydrocarbyl precursors which combine with the vinyl sulfonyl fluoride to form the portion $R^1$ of formulas I and II are olefins. These olefins include the cracked-wax alpha-olefins, the ethylene growth reaction alpha-olefins, and the high-molecular-weight, substantially saturated petroleum fractions and preferably substantially saturated olefin polymers, particularly polymers of monoolefins having from 2 to about 30 carbon atoms. Especially useful polymers are the polymers of 1-monoolefins such as ethylene, propene, 1-butene, isobutene, 1-hexene, 1-octene, 2-methyl-1-heptene, 3-cyclohexyl-1-butene, and 2-methyl-5-propyl-1-hexene. Polymers of olefins in which the olefinic linkage is not at the terminal position, are also useful. Such olefins are illustrated by 2-butene, 3-pentene, and 4-octene.

Also useful are interpolymers of olefins such as those illustrated above with other interpolymerizable olefinic substances such as other 1-olefins, aromatic olefins, cyclic olefins, and polyolefins. Such interpolymers include, for example, those prepared by polymerizing isobutene with styrene, isobutene and butadiene, propene with isoprene, ethylene with piperlyene, isobutene with chloroprene, isobutene with p-methyl styrene, 1-hexene with 1,3-hexadiene, 1-octene with 1-hexene, 1-heptene with 1-pentene, 3-methyl-1-butene with 1- octene, 3,3-dimethyl-1-pentene with 1-hexene, isobutene with styrene and piperylene, etc.

The relative proportions of the monoolefins to the other monomers in the interpolymers influence the stability and oil-solubility of the final compositions derived from such interpolymers. Thus, for reasons of oil-solubility and stability, the interpolymers contemplated for use in this invention should be substantially aliphatic and substantially saturated, i.e., they should contain at least about 80%, preferably at least about 95%, on a weight basis, of units derived from the aliphatic monoolefins and no more than about 20% of olefin linkages based on the total number of carbon-to-carbon covalent linkages. In most instances the percentage of olefinic linkages should be less than about 5 to 3% of the total number of carbon-to-carbon covalent linkages.

Specific examples of such interpolymers include copolymers of 95% (by weight) of isobutene with 5% styrene, terpolymer of 98% of isobutene with 1% of piperylene and 1% of chloroprene, terpolymer of 95% of isobutene with 2% of 1-butene and 3% of 1-hexene, terpolymer of 60% of isobutene with 20% of 1-pentene and 20% of 1-octene, copolymer of 80% 1-hexene and 20% of 1-heptene, terpolymer of 90% of isobutene with 2% of cyclohexene and 8% of propene, and copolymer of 80% of ethylene and 20% of propene.

Lower-molecular-weight olefins are also useful feedstocks, especially for the preparation of detergents, agricultural chemicals and medicinals. For these uses, olefins having the following formula are prepared:

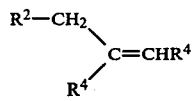

wherein $R^2$, $R^3$ and $R^4$ are independently hydrogen, an alkyl group of 1 to 20 carbon atoms, an alkenyl group of 3 to 20 carbon atoms, or a cycloalkyl group of 5 to 12 carbon atoms, and $R^2$ may be an aryl group of 6 to 12 carbon atoms, provided that the total number of carbon atoms in $R^2$, $R^3$ and $R^4$ is less than 21. The $R^2$ and $R^3$ or the $R^2$ and $R^4$ groups may be joined to form a 5- to 12-membered carbocyclic ring. Thus, $R^2$, $R^3$ and/or $R^4$ may be methyl, ethyl, n-propyl, n-butyl, octyl, decyl, octadecyl, eicosyl, isoamyl, 2-ethylhexyl, 4-methylpentyl, 10-methyldodecyl, 5-ethyltetradecyl, 2-propenyl, 5-hexenyl, 10-hexadecenyl, cyclopentyl, cyclohexyl, cyclodecanyl, 3-phenylpropyl, 4-(1-naphthyl)hexyl, etc. $R^2$ and $R^3$ together, or $R^2$ and $R^4$ together may be dimethylene, trimethylene, tetramethylene, 1,3-propenyl, etc., and $R^2$ may be phenyl, 2-naphthyl, etc.

Useful olefins include propene, butene-1, cis- and transbutene-2, 2-methylpentene-1, hexene-1, hexene-2, hexene-3, octene-1, dodecene-1, octadecene-1, eicosene-1, eicosene-2, 2-ethylhexene-1, 4-methylpentene-1, nonadecene-1, pentadiene-1,3, hexadiene-1,4, 2,4-dimethylhexadiene-1,3, cyclopentene, cyclohexane, beta-pinene, 1-methylcyclopentene, 1,3- and 1,4-cyclohexadiene, 1,2- and 1,4-dihydronaphthalene, 3-phenylpropene-1, cycloheptatriene, exomethylenecyclooctane, isobutene, and mixtures thereof, preferably a mixture of essentially straight-chain alphaolefins having from 10 to 20 carbon atoms.

The vinyl sulfonyl fluoride can be adducted to the olefinic hydrocarbyl precursor from the sources mentioned above by techniques similar to those used to adduct maleic anhydride to olefinic hydrocarbon substituents in the production of hydrocarbyl succinic anhydrides. This is surprising since no adduction occurs using vinyl sulfonyl chloride.

A fully satisfactory technique is to charge the olefinic hydrocarbyl substituent source to the reaction vessel and heat with stirring under pressure, if necessary. The vinyl sulfonyl fluoride is added to the reaction vessel and the reaction mass is heated to the reaction temperature, at which it is held for the duration of the reaction. The adduction is carried out at from about 100° to about 300° C., preferably 150° to 250° C. Generally the reaction will be complete in from about 1 to about 48 hours, and at the preferred reaction temperatures in about 2 to 24 hours. Generally, it has been found that the reactivity of the hydrocarbyl substituent source in the adduction reaction can be enhanced if it is first chlorinated. For example, an excellent hydrocarbyl substituent source is polyisobutylene. Polyisobutenyl chloride reacts faster and at lower temperatures than does polyisobutylene. The adducts can be purified by conventional techniques such as extraction with a lower alkanol, such as methanol, followed by vacuum distillation to remove light ends from the product.

Alternatively, the crude reaction mixture can be purified by codistillation with a hydrocarbon solvent of intermediate boiling range, such as a solvent-refined neutral oil. Preferably such a codistillation is carried out under reduced pressure, e.g., 100° C. at 2 mm Hg. Another method involves precipitation of insolubles by dilution with a lower-boiling hydrocarbon solvent, followed by filtration and stripping.

While it is preferable to have a hydrocarbyl group $R^1$ which contains a slight amount of unsaturation, e.g., 1 to 2 olefinic linkages, if a product having a completely saturated hydrocarbyl group is desired, it is necessary to hydrogenate the adduct or product with hydrogen, using a conventional noble metal oxide hydrogenation catalyst such as platinum or platinum oxide.

The hydroxycarbylethyl sulfonyl fluoride reacts readily with nitrogen-containing compounds containing at least

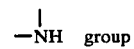

at low temperatures and in high yields. The nitrogen-containing compound must have at least one

to react with the sulfonyl fluoride to yield the sulfonamide product. A wide variety of nitrogen-containing compounds containing at least one primary or secondary amine group are useful for preparing sulfonamides of this invention. Suitable compounds include aliphatic and heterocyclic amines. These amines have the formula:

wherein $R^2$ and $R^3$ (A) each independently represent hydrogen or an organic radical bonded to the nitrogen through a carbon-to-nitrogen linkage such as hydrocarbyl, aminohydrocarbyl, alkoxyhydrocarbyl, alicyclic hydrocarbyl and alkylene polyamine-substituted hydrocarbyl, or (B) together with the N form a heterocyclic amine.

Preferably the aliphatic amines are selected from hydrocarbylamines, alkoxy-substituted hydrocarbylamines, and alkylene polyamines. Specific examples of hydrocarbylamines include methylamine, propylamine, butylamine, pentylamine, hexylamine, heptylamine, octylamine, di-n-butylamine, di-n-hexylamine, decylamine, dodecylamine, hexadecylamine, octadecylamine, etc. Specific examples of alkoxy-substituted hydrocarbyl amines include methoxyethylamine, butoxyhexylamine, propoxypropylamine, heptoxyethylamine, etc., as well as the poly(alkoxy)amines such as poly(ethoxy)ethylamine, poly(propoxy)ethylamine, poly(propoxy)propylamine and the like.

Examples of alkylene polyamines include alkylene polyamines

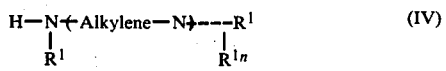 (IV)

wherein (A) n is an integer preferably of from 1–10; (B) each $R^1$ independently represents hydrogen or a substantially hydrocarbon radical; and (C) each Alkylene radical can be the same or different and is preferably a lower alkylene radical having 8 or less carbon atoms, and when Alkylene represents ethylene, the two $R^1$ groups on adjacent nitrogen atoms may be taken together to form an ethylene group, thus forming a piperazine ring.

In a preferred embodiment, $R^1$ represents hydrogen, methyl or ethyl. The alkylene amines include principally methylene amines, ethylene amines, propylene amines, butylene amines, pentylene amines, hexylene amines, heptylene amines, octylene amines, other polymethylene amines, and also the cyclic and the higher homologs of such amines such as piperazines and amino-alkyl-substituted piperazines. These amines are exemplified specifically by: ethylene diamine, diethylene triamine, triethylene tetraamine, propylene diamine, octamethylene diamine, di(heptamethylene) triamine, tripropylene tetramine, tetraethylene pentamine, trimethylene diamine, pentaethylene hexamine, di(trimethylene) triamine, 2-heptyl-3-(2-aminopropyl)-imidazoline, 4-methylimidazoline, 1,3-bis-(2-aminoethyl)-imidazoline, 1-(2-aminopropyl)-piperazine, 1,4-bis-(2-aminoethyl)-piperazine, and 2-methyl-1-(2-aminobutyl)-piperazine. Higher homologs such as are obtained by condensing two or more of the above-illustrated alkylene amines likewise are useful.

The ethylene amines are especially useful. They are described in some detail under the heading "Ethylene Amines" in *Encyclopedia of Chemical Technology*, Kirk and Othmer, Vol. 5, pages 898–905, Interscience Publishers, New York (1950). Such compounds are prepared most conveniently by the reaction of an alkylene chloride with ammonia. The reaction results in the production of somewhat complex mixtures of alkylene amines, including cyclic condensation products such as piperazines. Either the mixture or the pure alkylene amine may be used in the process of this invention. Tetraethylene pentamine is the preferred amine.

Additional alkylene polyamines useful for preparing the sulfonamides of this invention include those of the following formulas:

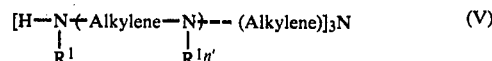 (V)

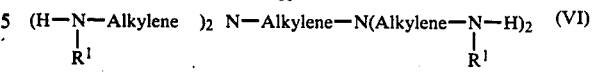 (VI)

wherein (a) n' is zero or an integer preferably less than about 10;

(b) each $R^1$ independently represents hydrogen or a substantially saturated hydrocarbon radical; and (c) each Alkylene radical can be the same or different, and is preferably a lower alkylene radical having 8 or less carbon atoms, and when Alkylene represents ethylene, the two $R^1$ groups on adjacent nitrogen atoms in Formula IV may be taken together to form an ethylene group.

These amines are exemplified by tris-(aminoethyl) amine, N,N,N',N'-tetra-(aminoethyl) ethylenediamine, and the like.

Suitable heterocyclic amines, in addition to the piperazines mentioned above in connection with the alkylene polyamines, include morpholines, imidazolines, aminoalkyl-substituted morpholines, and pyrrolidones such as aminoethyl pyrrolidone.

The oil-soluble sulfonamides of this invention are prepared by reacting at a temperature from 50° to 250° C. the hydrocarbylethyl sulfonyl fluoride with an organic nitrogen-containing compound containing at least one

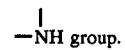 —NH group.

The oil-soluble sulfonamide product usually comprises from about 0.1 to about 1 equivalent of the amine-derived portion of the product per equivalent of the sulfonyl fluoride-derived portion.

In order to drive the reaction to complete, an excess of amine, usually from about 1.5 to 15 mols of amine per mol of sulfonyl fluoride, is beneficial. The excess amine can later be recovered. By using excess amine, up to about 1 equivalent of monoamine can be reacted with the sulfonyl fluoride. However, up to about 1.5 mols of polyamine per equivalent of sulfonyl fluoride can be incorporated possibly by solubilization into the sulfonamide composition. As mentioned above, the reaction between the hydrocarbylethyl sulfonyl fluoride and the nitrogen-containing compound is carried out at a temperature from about 50° to about 250° C., preferably from about 100° to about 200° C., and more preferably from about 125° to about 175° C. Typically the sulfonyl fluoride and the nitrogen-containing compound are liquid. Accordingly, the process can be conducted neat; however, inert solvents can be used. Suitable solvents include hydrocarbons such as refined mineral oil, as well as lower-boiling aliphatic and aromatic hydrocarbons, particularly those which have boiling points around the maximum temperature desired for the reaction.

Preferably the process is conducted under an inert atmosphere, nitrogen being readily available and the least expensive.

Ordinarily the reaction takes place in about 1 to about 24 hours.

The excess of the reactants as well as the hydrogen fluoride and any lower-boiling reaction solvents are removed by distillation, preferably at subatmospheric pressure.

Alternatively, the crude reaction mixture can be purified by codistillation with a hydrocarbon solvent of intermediate boiling range, such as a solvent-refined neutral oil. Preferably such codistillation is carried out under reduced pressure.

Subsequent to the sparging or codistillation operation, it is often desirable to dilute the sulfonamide with a suitable diluent in order to improve the handling characteristics of the reaction product. Typically about 25 to 50% weight diluent is added. Suitable diluents include solvent-refined neutral oils, particularly those having a low viscosity, e.g., about 100 SUS at 100° F. (38° C.).

Concentrated lubricating oil additive compositions ("additive concentrates") are provided within the scope of this invention comprising from about 90 to about 10% by weight of an oil of lubricating viscosity and from about 10 to about 90% by weight of the oil-soluble, nitrogen-containing composition prepared by reacting a hydrocarbylethyl sulfonyl fluoride with a nitrogen-containing compound containing at least one

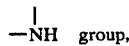
—NH group, in which the substantially saturated hydrocarbyl substituent contains at least 20 aliphatic carbon atoms. The concentrates provided by this invention should contain as much of the oil-soluble, nitrogen-containing composition as is practical, since the concentrates are prepared to reduce shipping costs, storage requirements, etc. Typically the concentrates contain only sufficient diluent to make them easy to handle during shipping and storage. Any inert diluent is suitable for the concentrates. Preferably the diluent is an oil of lubricating viscosity so that the concentrate may be readily mixed with lubricating oils when preparing lubricating oil compositions from the concentrate. Suitable lubricating oils which can be used as diluents typically have viscosities in the range from about 35 to about 1000 Saybolt Universal Seconds (SUS) at 100° F., although any oil of lubricating viscosity can be used.

Finished lubricating oil compositions can be prepared by combining such additive concentrates with lubricating oils. In a further embodiment of this invention, lubricating oil compositions are provided which comprise a major amount of an oil of lubricating viscosity and an amount effective to provide dispersancy of the oil-soluble, nitrogen-containing composition prepared by reacting a hydrocarbylethyl sulfonyl fluoride with a nitrogen-containing compound containing at least one amine hydrogen, i.e.,

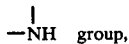
—NH group, in which the substantially saturated hydrocarbyl substituent contains at least 20 aliphatic carbon atoms.

Suitable lubricating oils which can be used to prepare a lubricating oil composition or concentrate of this embodiment are oils of lubricating viscosity derived from petroleum or synthetic sources. The oils can be paraffinic, naphthenic, halo-substituted hydrocarbons, synthetic esters or combinations thereof. Oils of lubricating viscosity have viscosities in the range 35 to 50 SUS at 100° F., and more usually from about 50 to 10,000 SUS at 100° F. The amount of the oil-soluble, nitrogen-containing composition of this invention which is incorporated in the lubricating oil composition to provide the effective amount necessary for dispersancy varies widely with the particular sulfonamide used, as well as the use to which the lubricating oil composition is put. Other conventional additives which can be used in combination with the sulfonamides include ashless dispersants such as the type disclosed in U.S. Pat. Nos. 3,172,892, 3,219,666, and 3,381,022. Neutral and basic calcium, barium and magnesium petrosulfonates or alkylphenates, oxidation inhibitors, antifoam agents, viscosity index improvers, pour point depressants, and the like, such as chlorinated wax, benzyl disulfide, sulfurized sperm oil, sulfurized terpene, phosphorus esters such as trihydrocarbon phosphites, metal thiocarbamates such as zinc dioctyl dithiocarbamate, metal phosphorus dithioate, such as zinc dioctyl phosphorodithioate, polyisobutylene having an average molecular weight of 100,000, etc.

In general, the lubricating oil compositions will contain from about 0.1 to about 10% by weight of the oil-soluble nitrogen-containing composition prepared from the hydrocarbylethyl sulfonyl fluoride and the amine containing at least one

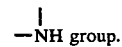
—NH group.

More usually the lubricating oil composition of the invention will contain from about 0.5 to about 10% by weight, and more usually from about 1 to about 8% by weight, of the nitrogen-containing composition prepared from the hydrocarbylethyl sulfonyl fluoride and the organic compound containing at least one

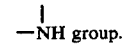
—NH group.

Alternatively, in some instances it is desirable to prepare concentrated lubricating oil additive compositions, that is additive concentrates (containing up to 90% by weight the oil-soluble nitrogen-containing compositions of this invention prepared from hydrocarbylethyl sulfonyl fluoride.

The lubricating oil compositions of this invention is useful for lubricating internal combustion engines. The lubricating oils not only lubricate the engines, but because of their dispersancy properties, help maintain a high degree of cleanliness of the lubricated parts.

Those lubricating oils containing sulfonamides of this invention wherein the R¹ group contains from 20 to about 35 carbon atoms are particularly useful as lubricants in two-cycle engines.

The sulfonamides of this invention find additional utility as fuel additives, in which capacity from 0.000001 to 5% by weight sulfonamide is employed. When employed in normally liquid petroleum distillate fuels, e.g., fuel oils, diesel oils, gasolines, aviation gasolines, jet fuels, etc., they promote engine cleanliness, particularly of the fuel systems such as fuel lines, carburetors, injectors, pumps, and the like. In furnace fuel oils, for example, they serve as antiscreen-clogging agents.

The hydrocarbylethyl sulfonic fluorides prepared from the 5 to 25 carbon, preferably 10 to 20 carbon atom alpha-olefins are readily converted to the sodium salt of primary paraffin sulfonic acids by saponification with sodium hydroxide. Preferably this reaction is carried out by mixing the fluoride with an aqueous caustic solution of about 10 to 50% concentration, and heating, under reduced pressure if necessary, at a temperature in the range of 75° C. to 175° C. for 25 to 200 minutes. The resulting primary paraffin sulfonate after hydrogenation is essentially the same product as that described in U.S. Pat. No. 3,150,169, and is an excellent material for making detergent bars.

EXAMPLES

The following examples are included to further illustrate the invention.

EXAMPLE 1

(a) Preparation of Chloroethyl Sulfonyl Chloride

To a 5-liter, 3-necked flask is added 747 ml of 2-mercaptoethanol. The reaction vessel is cooled to between 0° to 5° C. and maintained at this temperature while chlorine gas is added at the rate of 185 g per hour. After 1205 g of chlorine has been added, the remaining 1205 g chlorine is added while 198 g of distilled water is also being added. A total of 2415 g of chlorine is added over a 14-hour period. After all the chlorine is added, the reaction mixture is warmed up while sparging with nitrogen to remove free chlorine.

EXAMPLE 1

(b) Preparation of Chloroethyl Sulfonyl Fluoride

To 1731.6 g of chloroethyl sulfonyl chloride in a 5-liter reaction vessel under nitrogen with stirring and cooled with a water bath is added a solution of 923.8 g anhydrous potassium fluoride in 1 liter distilled water, dropwise. During the addition of the aqueous potassium fluoride, the temperature, even with cooling in a water bath, increases to 65° to 70° C. The reaction mixture is heated to 100° C. and refluxed for 15 minutes. The solids are removed by filtration and then washed with dichloromethane. The combined organic layers are placed in a separatory funnel and the upper layer is removed and discarded. The bottom layer, combined with the dichloromethane wash, was placed in a 5-liter reaction vessel and stripped under vacuum to yield 1325 g of chloroethyl sulfonyl fluoride.

EXAMPLE 1

(c) Preparation of Vinyl Sulfonyl Fluoride

To a 5-liter reaction vessel containing 1325 g of chloroethyl sulfonyl fluoride is added 2286 ml of distilled water, followed with stirring by the addition of 201.5 g magnesium oxide. The temperature of the reaction mixture increases to 40° C. The reaction mixture is then heated to 60° C., cooled to room temperature and then again heated to 40° C. for ¼ hour. The reaction mixture is separated in a separatory funnel and the organic layer dried over magnesium sulfate. Water and methylene chloride are added and the aqueous portion is separated. The methylene chloride portion is filtered through diatomaceous earth. This solution is then dried over magnesium sulfate and filtered and stripped under vacuum. The product is purified by distillation to yield 364.2 g vinyl sulfonyl fluoride, b.p. (overhead) 110°–118° C.

EXAMPLE 2

Adduction of Vinyl Sulfonyl Fluoride to Polyisobutylene

To a large bomb is charged 192 g of polyisobutylene having a number of average molecular weight of 950 and 19.2 ml of vinyl sulfonyl fluoride. The mixture is heated to 210° C. at 85 pounds pressure with shaking. The temperature is maintained for 16 hours while the pressure has increased to 100 pounds. The reaction mixture is allowed to cool and then transferred to a 500-ml flask. Vacuum stripping is used to remove the vinyl sulfonyl fluoride. The product is filtered twice through diatomaceous earth to yield 164.5 g of polyisobutenyl sulfonyl fluoride containing 1.3% sulfur and 0.69% fluorine. Infrared confirms that the material is predominantly polyisobutenyl sulfonyl fluoride.

EXAMPLE 3

Preparation of Sulfonamide from Triethylene Tetramine

To a 100-ml flask is added 15 g of polyisobutenyl sulfonyl fluoride prepared in Example 2 and 10 ml of benzene. The mixture is stirred until all the materials dissolve, and then a solution of 2.2 g of triethylene tetramine in 5 ml of benzene is added. The reaction mixture is heated in a water bath for 2½ hours. After cooling, hexane is added to the reaction mixture, which is then filtered through diatomaceous earth. Aqueous potassium carbonate solution is added and the mixture is heated to reflux for 1 hour. The mixture is cooled and allowed to stand overnight. Upon standing, it separates into two layers. The aqueous layer is separated and the hexane layer is stripped on a rotary evaporator. Toluene is added and water is removed by azeotropic distillation. The product, 11.5 g, contains 1.9, 1.36% sulfur, 1.8, 1.47% nitrogen.

EXAMPLE 4

Preparation of Sulfonamide from Tetraethylene Pentamine and Polyisobutenyl Sulfonyl Fluoride Following the procedure of Example 3, 2.9 g of tetraethylene pentamine is reacted with 15 g of polyisobutenyl sulfonyl fluoride prepared in Example 2. The product is 11.6 g of predominantly the polyisobutenyl sulfonamide of tetraethylene pentamine having an analysis of 0.95, 0.95% sulfur and 2.21, 2.21% nitrogen.

Similarly, following the procedures of the above examples, products can be prepared by reacting any one of the following hydrocarbyl precursors with vinyl sulfonyl fluoride:

polypropylene
ethylene-propylene copolymers
polybutene

These products can be converted to sulfonamide lubricating oil additives by reacting with, for example:

morpholine
bis-N,N'-aminopropyl ethylene diamine
dimethylaminopropyl amine
piperazine
ethylene diamine

EXAMPLE 5

Alternative Preparation of Chloroethyl Sulfonyl Chloride

Chloroethylsulfonic chloride may also be prepared by charging 500 grams (3.38 mols) of the sodium salt of isethionic acid to a 3-liter, 3-necked flask containing 315 ml of dimethylformamide and 600 mls of dichloromethane. To this mixture 1216 grams of thionyl chloride was added dropwise. After all of the thionyl chloride was added, the reaction mixture was heated at 40°–60° C. until the evolution of gases ceased. It was then poured over 2 liters of ice. After warming to room temperature, the layers were separated and the bottom layer was washed with water. This washed product was then dried over magnesium sulfate. When dry, the sulfate was removed by filtration and the dichloromethane was removed by distillation to leave 505 g of crude product. This crude product was readily converted to chloroethyl sulfonyl fluoride by treatment with potassium fluoride as in Example 1(b).

What is claimed is:

1. Compounds having the formula

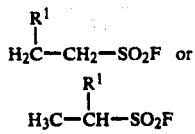

wherein $R_1$ is a polymeric 1-olefin-derived hydrocarbyl group of from 50 to 150 carbon atoms with 1 to 3 double bonds.

2. A process for the preparation of hydrocarbylethyl sulfonyl fluorides of the formula:

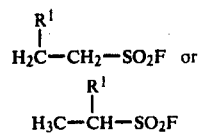

wherein $R^1$ contains about 3 to 350 carbon atoms consisting essentially of reacting vinyl sulfonyl fluoride with an unsaturated hydrocarbyl precursor selected from the group consisting of; an olefin of the formula:

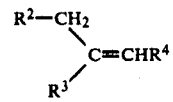

wherein $R^2$ is hydrogen, an alkyl group of 1 to 20 carbon atoms, an alkenyl group of 3 to 20 carbon atoms, a cycloalkyl group of 5 to 12 carbon atoms, or an aryl group of 6 to 12 carbon atoms, $R^3$ and $R^4$ are independently hydrogen, an alkyl group of 1 to 20 carbon atoms, an alkenyl group of 3 to 20 carbon atoms or a cycloalkyl group of 5 to 12 carbon atoms, provided that the total number of carbon atoms in $R^2$, $R^3$ and $R^4$ is less than 21, or $R^2$ may be joined to either of $R^3$ or $R^4$ to form a 5 to 12 membered carbocyclic ring; an olefin polymer or copolymer, at a temperature of from 100° to 300° C.

3. The process according to claim 2 wherein the hydrocarbylethyl sulfonyl fluoride contains from 5 to 25 carbon atoms.

4. The process according to claim 2 wherein the hydrocarbyl group contains from 25 to 250 carbon atoms.